United States Patent
Dahlgren (10) Patent No.: US 7,916,301 B2
(45) Date of Patent: Mar. 29, 2011

(54) FILTER DESIGN FOR COLORIMETRIC MEASUREMENT

(75) Inventor: Brett E. Dahlgren, Albany, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 270 days.

(21) Appl. No.: 12/251,137

(22) Filed: Oct. 14, 2008

(65) Prior Publication Data

US 2010/0091286 A1    Apr. 15, 2010

Related U.S. Application Data (60) Provisional application No. 61/079,655, filed on Jul. 10, 2008.

(51) Int. Cl.
*G01J 3/45* (2006.01)
*G01B 9/02* (2006.01)

(52) U.S. Cl. .................. 356/454; 356/519

(58) Field of Classification Search ........... 356/454, 356/480, 519
See application file for complete search history.

(56) References Cited

U.S. PATENT DOCUMENTS

| | | | |
|---|---|---|---|
| 5,144,498 A * | 9/1992 | Vincent ............... | 359/885 |
| 5,202,939 A | 4/1993 | Belleville et al. | |
| 5,272,518 A * | 12/1993 | Vincent ............... | 356/405 |
| 6,295,130 B1 | 9/2001 | Sun et al. | |
| 6,349,156 B1 | 2/2002 | O'Brien et al. | |
| 6,381,022 B1 | 4/2002 | Zavracky | |
| 7,009,716 B2 | 3/2006 | Kim et al. | |
| 7,330,266 B2 | 2/2008 | Guerineau et al. | |
| 7,417,735 B2 * | 8/2008 | Cummings et al. ........ | 356/408 |
| 2005/0046868 A1 | 3/2005 | Kim et al. | |
| 2006/0132787 A1 | 6/2006 | Mestha et al. | |
| 2006/0290933 A1 | 12/2006 | Holm | |
| 2007/0153288 A1 | 7/2007 | Wang et al. | |
| 2010/0091286 A1 * | 4/2010 | Dahlgren ............... | 356/416 |

FOREIGN PATENT DOCUMENTS

JP    2000031510    1/2000

* cited by examiner

*Primary Examiner* — Patrick J Connolly (57) ABSTRACT

A color detector includes a light source configured to generate light with a spectrum of wavelengths; a plurality of filters in optical communication with the light source, wherein each filter is configured to pass a bandwidth of wavelengths around a different peak wavelength; and a plurality of photodetectors, each configured to receive light passed through a respective filter of the plurality of filters. The bandwidth of each filter is configured to Correspond to a bandwidth of a curve from a set of standard color matching functions. A method for improving color detection accuracy in a color detector includes matching a bandwidth passed by each of a plurality of color filters with a bandwidth and peak wavelength of a Commission Internationale de l'Eclairage (CIE) color matching function; and separately detecting an amount of light passed by each the filter.

20 Claims, 6 Drawing Sheets

FILTER DESIGN FOR COLORIMETRIC MEASUREMENT

CROSS REFERENCE TO RELATED APPLICATIONS

This Application claims the benefit of U.S. Provisional Application Ser. No. 61/079,655, filed Jul. 10, 2008, titled "Filter Design For Colorimetric Measurement" which is hereby incorporated by reference herein as if reproduced in full below.

BACKGROUND

In various applications including televisions, projectors, monitors, camcorder viewfinders, printing devices, and other applications that detect or project colors, a spectrophotometer or calorimeter may be used to detect and measure a spectrum of colors. Colorimeters may determine colors using one or more sets of photodetectors and color filters each configured to detect a predetermined spectrum of wavelengths. The filters often have similar bandwidths and generally are chosen so that they span the visible spectrum.

However, the resulting performance of many such filters does not correspond well to the response of Commission Internationale de l'Eclairage (CIE) observer color-matching functions at all wavelengths. The lack of correspondence at a given wavelength can be quite large, particularly for spectra that vary rapidly with wavelength or spiky spectra.

Some calorimeters use few photodiodes and filters to determine colors and consequently require that the filter responses closely correspond with the color-matching functions for accurate color detection. The expense of these filters increases with increased correspondence to the standard. Other colorimeters use more filters of narrower, but similar, bandpass to cover the visible spectrum.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

The present specification discloses systems and methods related to the determination of color in devices capable of projecting or detecting color and the improvement of accuracy of such systems.

As used in the present specification and in the appended claims, the term "colorimeter" refers to an instrument used to measure the emission, absorption or reflection of light by a given material or to calibrate devices that output color images, printing, or illumination. Colorimeters generally include at least a photodetector and a filter and may also include a light source.

The term "photodetector" refers to a device that converts light or optical energy to electrical energy. Such a device may be, but is not limited to, a photodiode, phototransistor, avalanche photodiode, phototube, photovoltaic cell, or any device capable of converting optical energy to electrical energy known in the art.

As used in the present specification and in the appended claims, the term "color-matching functions" refers to a set of functions that describe the chromatic response of a standard observer or detector at a standard reference point. The color-matching functions may be thought of as the spectral sensitivity curves of three linear light detectors that yield tristimulus values in a three-component color model, which when added together, describe a specified color sensation. The three color-matching functions are generally referred to as "x-bar," "y-bar," and "z-bar." International standard color-matching functions have been established by the Commission Internationale de l'Eclairage (CIE), or International Commission on Illumination.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an embodiment," "an example" or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Figure 1:
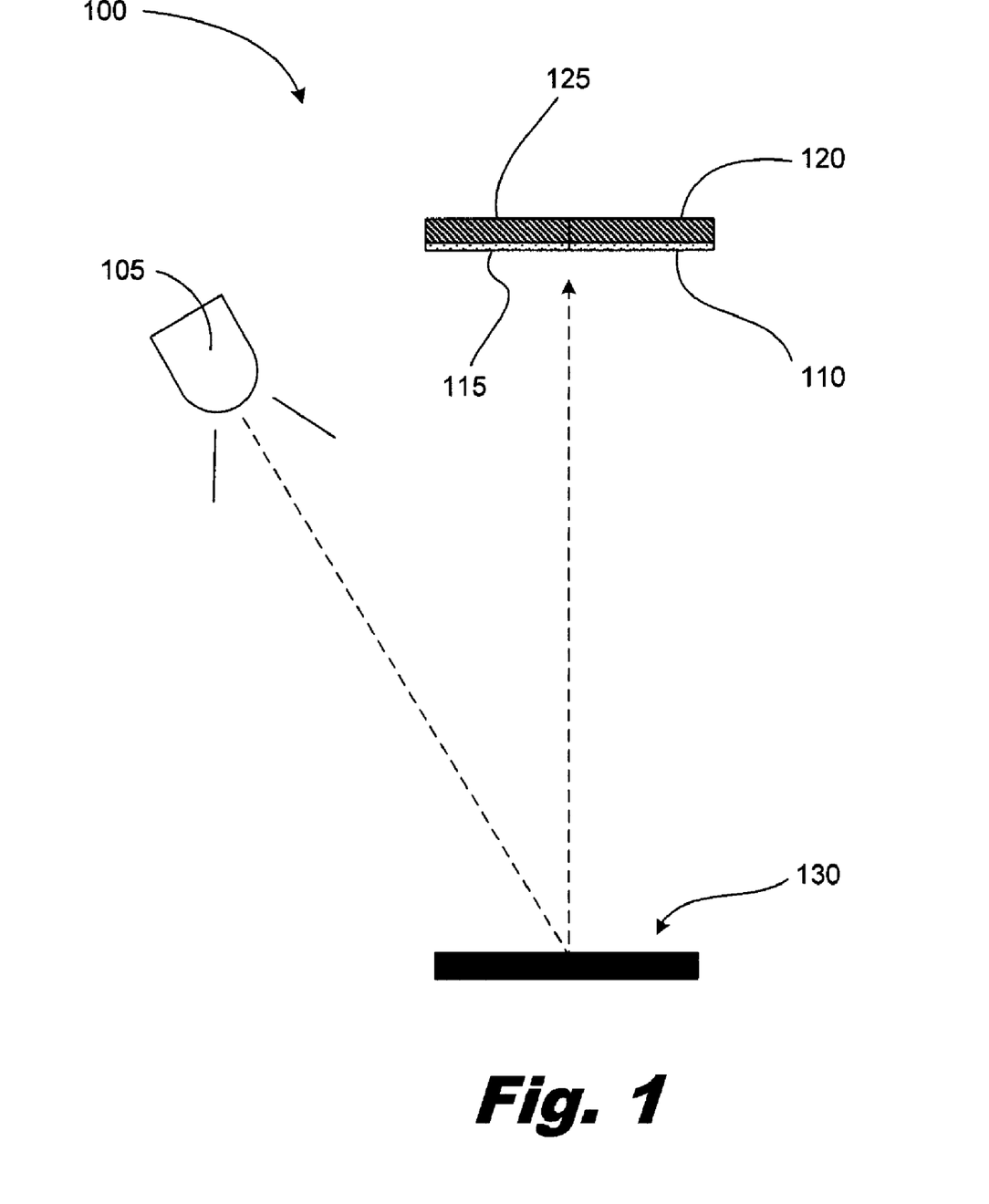
FIG. 1 is a cross-sectional diagram of one embodiment of an illustrative color detector according to principles described herein.

FIG. 1 shows an illustrative embodiment of a basic calorimeter (100). The illustrated colorimeter includes a light source (105), a plurality of filters (110, 115), and corresponding photodetectors (120, 125) associated with respective filters (110, 115). In the illustrated embodiment, the two photodetectors (120, 125) and corresponding filters (110, 115) are arranged side-by-side.

The light source (105) projects light onto a material (130), which may absorb some wavelengths of the light, depending on the molecular and/or chemical composition of the material (130). The material (130) may then reflect a portion of the light toward the filters (110, 115) and photodetectors (120, 125). Any light falling with a spectrum of wavelengths corresponding to the bandpass of one of the filters (110, 115) may pass through the respective filter.

For example, if a first filter (110) has a bandpass of a first spectrum of wavelengths, and a second filter (115) has a bandpass of a second spectrum of wavelengths different from the first spectrum of wavelengths, light with a wavelength falling within the first spectrum passes through the first filter (110), but is at least substantially blocked by the second filter (115). Similarly, light with a wavelength falling within the second spectrum passes through the second filter (115), but is at least substantially blocked by the first filter (110). Alternatively, if the first and second spectra of wavelengths overlap each other, a portion of the light falling within the overlap may pass through both the first and the second filters (110, 115), while light falling outside of the overlap either gets passed through only the first filter (110) or only the second filter (115) if it falls within the first spectrum or second spectrum, respectively.

The first filter (110) is positioned between the material (130) and the first photodetector (120). Likewise, the second filter (115) is positioned between the material (130) and the second photodetector (125). Consequently, only light that passes through one of the filters (110, 115) reaches the respective photodetector (120, 125).

Due to the filters (110, 115) placed in front of the photodetectors (120, 125), the first photodetector (120) is only able to convert light within the first spectrum of wavelengths from an optical signal to an electrical signal, and the second photodetector (125) is only able to convert light within the second spectrum of wavelengths from an optical signal to an electrical signal. Each photodetector (120, 125) produces an electrical signal which may be interpreted by a processor or other circuitry to determine the intensity of the light within each spectrum of wavelengths.

The intensity of the light indicates the amount of light within the specified spectrum that is present. The intensity of light that passes through a filter is proportional to the electrical signal produced by the photodetector under that filter. Thus, if light reflected by the material (130) has more light within the first spectrum of wavelengths than the second spectrum of wavelengths, the first photodetector (120) will produce a greater electrical signal than the second photodetector (125) because more light will pass through the first filter (110). Consequently, the processor may then analyze and compare the electrical signals produced by the photodetectors (120, 125) and determine the hue, saturation, and/or brightness of the reflected light.

The strength of the generated electrical signal may also vary depending on the inherent characteristics of each wavelength of light. Additionally, transmission characteristics of the filters (110, 115) or conversion efficiency of the photodetectors (120, 125) may vary depending on each individual spectrum of wavelengths. Thus, the filters (110, 115) or photodetectors (120, 125) may be configured accordingly such that spectra having different wavelengths and equal intensity may each result in electrical signals of equal magnitude. The area of the photodetectors (120, 125) or filters (110, 115) may be adjusted to achieve this result. The signal-to-noise ratio of each of the photodetectors (120, 125) may also be optimized accordingly.

Figure 2:
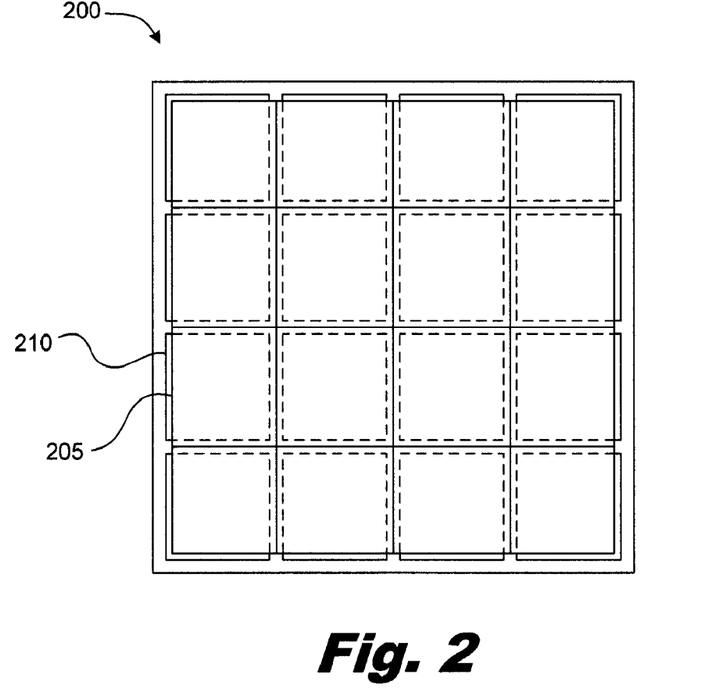
FIG. 2 is a diagram of one embodiment of an illustrative array of photodetectors and filters according to principles described herein.

As shown in the embodiment of FIG. 2, a colorimeter (100) may include an array (200) having any number of filters (205) that pass different wavelength bands to corresponding photodetectors (210). More filters (205) and photodetectors (210) may allow for a higher degree of accuracy of the color detection, though it may also result in a higher overall cost for the calorimeter (100).

The filters (205) may be configured to allow predetermined spectra of wavelength to pass. While each filter (205) may allow a negligible amount of every range of wavelengths from the entire visible spectrum, which ranges from about 380 nanometers (nm) to 750 nm, the filters (205) may allow spectra having different peak wavelengths such that substantially all of the light passing through each filter (205) is at or proximate the respective peak wavelength.

As discussed previously, the relative area of the filters (205) or photodetectors (210) may be adjusted according to the spectrum to which each filter (205) and photodetector (210) is specifically configured. Consequently, each of the filter (205) and photodetector (210) pairs may have substantially similar areas, as is depicted in FIG. 2, or they may have different areas to account for different properties associated with each spectrum of wavelengths.

The array (200) of filters (205) and photodetectors (210) may be part of an integrated circuit. In the current embodiment, 16 photodetectors (210) are paired with 16 filters (205). Each of the filters (205) may be configured to pass a different range of wavelengths. The outputs of the photodetectors (210) may be multiplied by a 16×3 matrix to produce a color coordinate of the light reaching the photodetectors (210). This matrix may be determined by finding polynomial fits where a first set of vectors of values includes the spectral responses of the 16 filters and a second set of vectors includes the CIE color-matching functions. The first and second vector sets may be paired by wavelength.

Figure 3:
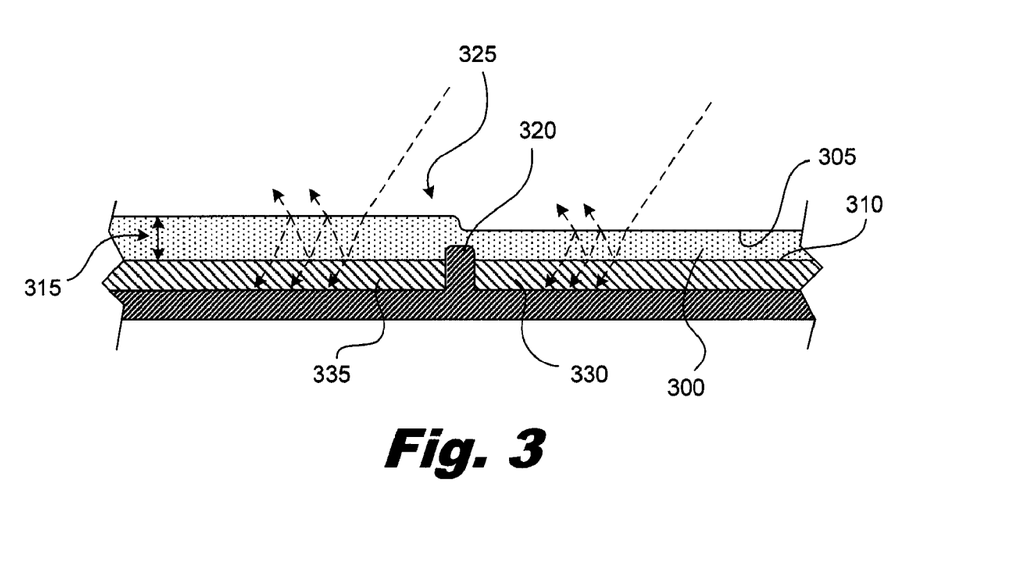
FIG. 3 is a cross-sectional diagram of one embodiment of an illustrative filter layer and a plurality of photodetectors according to principles described herein.

In some embodiments, an entire array of filters may be made from a single, connected layer (300). For example, a filter may be a Fabry-Perot etalon, as illustrated in the embodiment of FIG. 3. A Fabry-Perot etalon is a transparent layer or plate with two partially reflecting surfaces. Light is allowed to pass through the etalon depending on whether internal reflections within the etalon are in phase or out of phase.

Light will pass through an upper surface (305) of the etalon and reflect between the upper surface (305) and a lower surface (310) before potentially exiting through the lower surface (310). This is known as internal reflection. Internal reflections that are in phase will constructively interfere until they pass through the filter. On the other hand, internal reflections that are out of phase will negatively interfere with themselves and will die out before passing through the filter.

The spectrum of wavelengths allowed to pass through the etalon may be dependent on factors such as the wavelength of the light, the angle the light travels through the etalon, the thickness of the etalon or the distance between the upper and lower reflective surfaces, and the refractive index of the material from which the etalon is made.

One simple way of changing the bandpass spectrum of a Fabry-Perot etalon is to change its thickness. Thus, a plurality of Fabry-Perot etalons with different bandpass spectra may be fabricated from a single layer (300) by varying a thickness (315) of the layer (300) for each filter. Varying the layer thickness (315) may be done with a minimum of masking steps during fabrication on a wafer, which helps simplify production of the filters. Colorimeters fabricated in this manner may be integrated with other circuitry for use in microelectrical systems.

A plurality of layers may also be used to make a similar filter that operates on the same principles, such as in a Fabry-Perot interferometer. A Fabry-Perot interferometer uses two parallel, partially reflecting layers spaced a distance apart in order to filter light. The thickness of each layer may be varied over each layer, as may the distance between both layers, to make a plurality of interferometers. Additionally, the refractive index of a material between the two parallel layers may affect the spectrum allowed to pass through the filter, and may be adjusted during fabrication to allow a predetermined spectrum to pass.

A separator (320) may be disposed between each of the photodetectors after fabrication to, for example, prevent light from a first filter (305) adjacent a first photodetector (330) from being received by a second photodetector (335). Otherwise, the output of the second photodetector (335) will not uniquely represent the wavelengths passed by the filter associated with that second photodetector (335). The separator (320) may extend into the layer (300) of filters in order to effectively block reflections.

Figure 4:
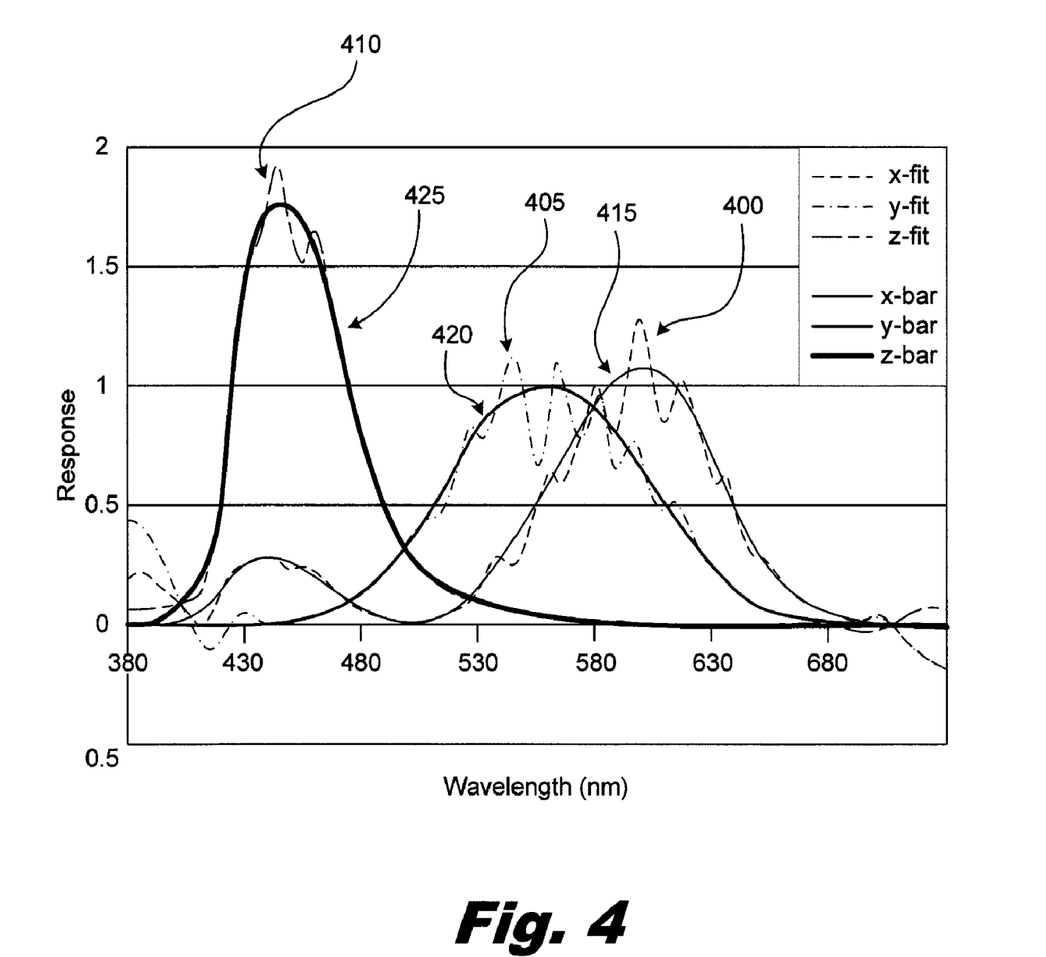
FIG. 4 is a graph of illustrative responses of Commission Internationale de l'Eclairage (CIE) color-matching functions and corresponding filter responses according to principles described herein.
Figure 5:
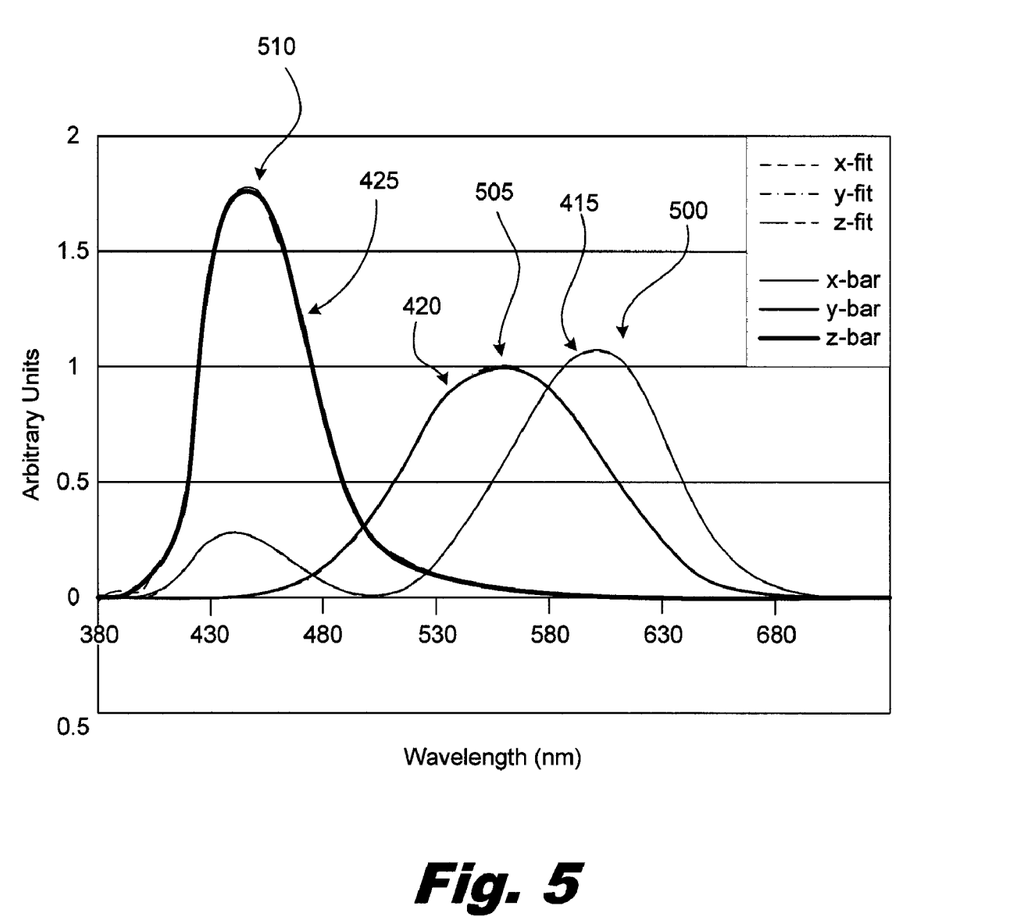
FIG. 5 is a graph of illustrative responses of Commission Internationale de l'Eclairage (CIE) color-matching functions and corresponding filter responses according to principles described herein.

FIGS. 4 and 5 are graphs showing illustrative examples of fitted responses of photodetectors (210) with filters (205) optimized for use as a spectrophotometer compared to the ideal responses (415, 420, 425) of the color-matching functions. Each of the three color-matching functions has a dominant wavelength or range of wavelengths where the response is greater than at other wavelengths.

The z-bar function response (425) has a dominant range at a lower end of the visible spectrum, the y-bar function response (420) has a dominant range approximately in the middle of the visible spectrum, and the x-bar function response (415) has a dominant range above the middle of the visible spectrum. The x-bar function response (415) also includes a secondary range toward the lower end of the visible spectrum, but the secondary range has a significantly lower response value than the z-bar function response (425).

The example in FIG. 4 shows illustrative fitted responses (400, 405, 410) of photodetectors (210) for Fabry-Perot filters having about a 20 nm full-width-at half-maximum (FWHM) bandpass, though the filters may have any FWHM bandpass range of wavelengths. FWHM defines a waveform based on the difference between two extreme values of the waveform at half of the waveform's maximum amplitude.

The total error of the fitted responses to the ideal response of the color-matching functions may be determined by taking the absolute difference between the fitted response and the ideal response at specified intervals (such as equal 1 nm intervals) and summing them over the visible spectrum. The general trend of the fitted response in FIG. 4 follows the ideal response, but the many deviations produced by the filters cause large, localized errors. Such a response may be suitable for a colorimeter measuring spectra that vary slowly with wavelength, but would be unsuitable for spiky spectra because it may potentially produce readings with large errors or deviations from the CIE responses. Errors in the responses can result in differences between the actual colors and the detected colors, such as detecting the wrong hue, brightness, or intensity of the colors.

FIG. 5 shows significantly improved fitted responses (500, 505, 510) that more closely match the ideal responses (415, 420, 425) of the color-matching functions and allow tolerance for processing variation in the light reaching the photodetectors. Improved matching of the filter bandpass to the bandpass of the CIE color-matching functions may be obtained by increasing the bandpass of the filters using different materials or by using lower order responses of the Fabry-Perot filters. The bandwidth of the filters is particularly important for tailoring the filter responses to match the characteristic curves of the CIE color-matching functions. The closer the bandwidth of the filters is to the bandwidth of the color-matching functions, the better the approximation. The dominant wavelengths (peaks) of the filters may not need to be matched exactly with the peaks of the color-matching functions if there are enough filters to span the whole response of the color-matching functions within the visible spectrum.

The second order Fabry-Perot response is narrower than the first order response, so second order filters may be used for the z-bar function at the lower (blue) end of the visible spectrum. By using Fabry-Perot second order responses of the photodetectors corresponding to the z-bar color-matching function, and first order responses of the photodetectors corresponding to the x-bar and y-bar color matching functions, the total error may be reduced to a fraction of the total error in the example of FIG. 4.

Due to the use of second order filters for the z-bar function, more filters (205) and photodetectors (210) may be needed to produce a good fit to the ideal response. In some embodiments, the number of filters (205) and photodetectors (210) corresponding to the z-bar function may be equal or relatively similar to the number of filters and photodetectors corresponding to the x-bar and y-bar functions combined. There may be some overlap between the first and second order filters. If the overlap is increased by changing the time of the etch that determines the difference of layer thickness (315) between the first and second order filters, the match between the fitted response and the ideal response improves, and color measuring performance increases.

Second order Fabry-Perot filters may be accomplished by changing the depositions and etches used to fabricate the photodetectors on a wafer without adding additional cost to fabrication, because the changes may only include a new start position and set of spacings for fabrication. While both first and second order filters may not provide a perfect fit for respective color-matching functions, implementing a plurality of filters for each of the x-bar, y-bar, and z-bar response may provide a sufficiently accurate fit, as long as there are enough filters to span the responses of the color-matching functions.

Lossy reflectors such as aluminum may be used in first order Fabry-Perot filters to improve the performance. The filters (205) may include a plurality of layers (300) in a stack, and each of the layers (300) of the stack has a thickness (315) which may be configured or adapted to achieve a desirable response for the filters (205), particularly for fitting the z-bar function response (425). However, varying more than one layer (300) of the stack may increase production costs.

The configuration of the photodetectors (210) and filters (205), including the centering and spacing of the thickness (315) of the filters (205) may be analyzed using Monte Carlo optimization, which relies on repeated random sampling to compute results. Optimization is done to provide the lowest error given manufacturing tolerances for the specific photodetectors and filters. This method may be helpful due to uncertainty in the amount and characteristics of light passing through the filters (205) that may exist, though any other method or combination of methods of analysis may be employed to optimize the spacing and centering of the thickness (315) of the filters (205) to improve the yield performance of each of the individual photodetectors, and consequently the colorimeter (100).

Figure 6:
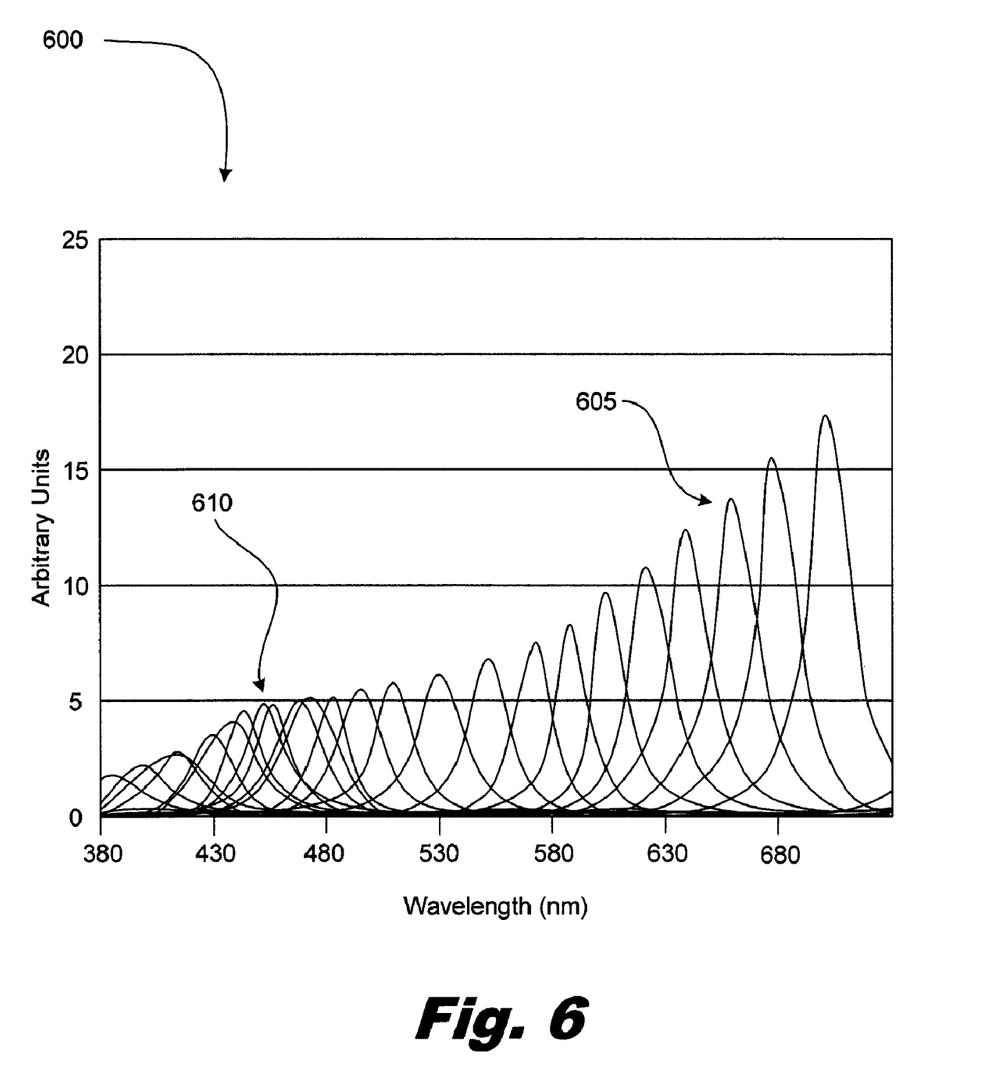
FIG. 6 is a graph of one embodiment of illustrative filter sets spanning a visible spectrum according to principles described herein.

FIG. 6 is a graph (600) illustrating the bandpass spectra of one embodiment of a set of filters (205) with narrow bandwidths. One example of a material used in filters having a narrow bandwidth may be silver. The filter set may have a higher response at longer wavelengths in the visible spectrum, as in the current embodiment, or it may have a higher response at lower wavelengths or at any other region of the visible spectrum. Some of the filters may have a primary dominant range (605) of wavelengths in one region of the visible spectrum and have a secondary range (610) of wavelengths in another region of the visible spectrum. The secondary range (610) of one filter may overlap the primary dominant range (605) of another filter. The filter set may include more than one filter sharing a similar primary dominant range (605) or secondary range (610).

Figure 7:
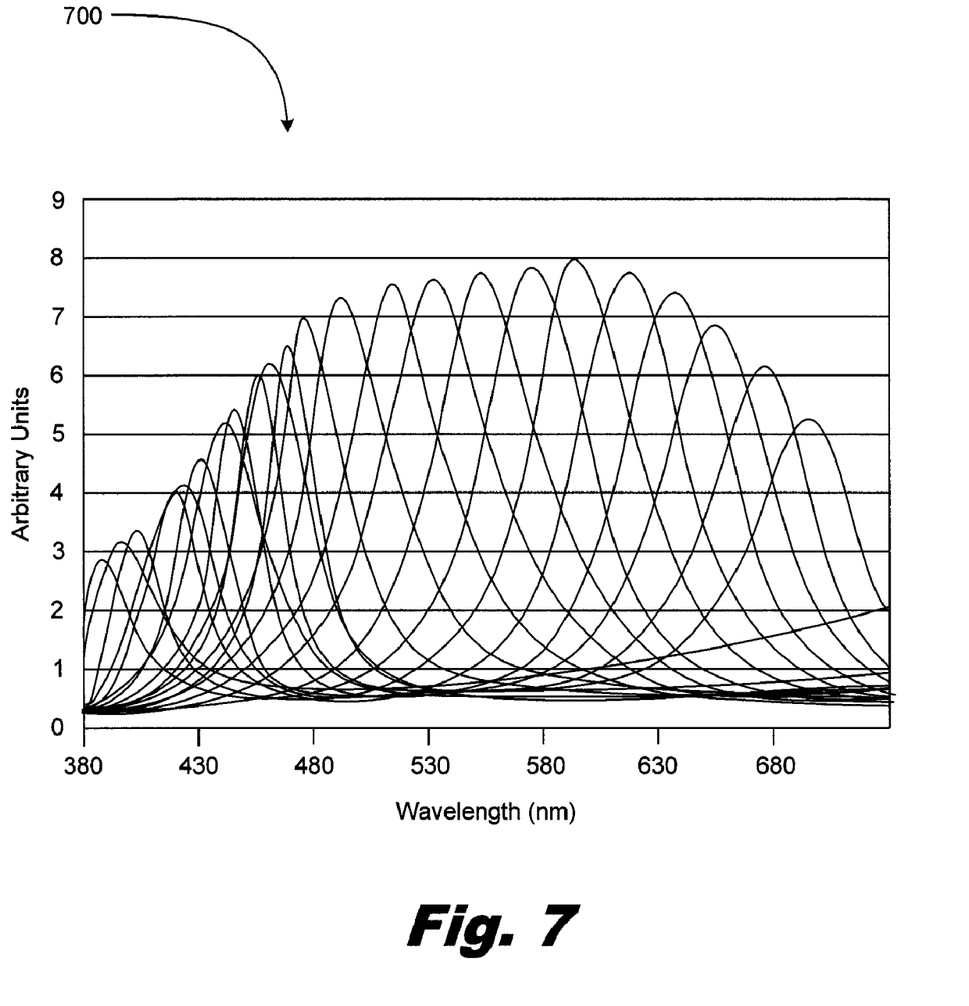
FIG. 7 is a graph of illustrative filter sets spanning a visible spectrum according to principles described herein.

FIG. 7 is a graph (700) illustrating the bandpass spectra of an embodiment of a set of filters (205) with wider bandwidths than those in FIG. 6. The wider bandwidth may provide a better match for one or more of the color-matching functions. One example of a material used in filters having a wide bandwidth may be a lossy reflector, such as aluminum as mentioned previously. Second order aluminum Fabry-Perot filters may be used to match the z-bar color-matching function. The set of filters may also have two ranges of bandwidths, including a range of bandwidths from first order filters and a range of bandwidths from second order filters. The first and second order filters may or may not overlap, depending on the filters used in the calorimeter. The fitted response for overlapped filters may be different than the fitted response for filters with no overlap between the first and second order filters.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A color detector, comprising:
   a light source configured to generate light with a spectrum of wavelengths and direct that light onto a object to illuminate said object;
   a plurality of filters receiving light from said object, wherein each filter is configured to pass a bandwidth of wavelengths around a different peak wavelength; and
   a plurality of photodetectors, each configured to receive light passed through a respective filter of said plurality of filters;
   wherein said bandwidth of each filter is configured to correspond to a bandwidth of a curve from a set of standard color matching functions.

2. The color detector of claim 1, wherein said standard color matching functions are Commission Internationale de l'Eclairage (CIE) color-matching functions.

3. The color detector of claim 1, wherein said filters are fabricated from a single layer.

4. The color detector of claim 1, wherein said filters are Fabry-Perot filters.

5. The color detector of claim 1, wherein said filters comprise a lossy reflector.

6. The color detector of claim 5, wherein said lossy reflector comprises aluminum.

7. The color detector of claim 1, wherein said filters include first order and second order filters.

8. The color detector of claim 7, wherein said first order filters are matched to responses of x-bar and y-bar functions of said color-matching functions.

9. The color detector of claim 7, wherein said first order filters and said second order filters overlap.

10. The color detector of claim 7, wherein said second order filters are matched to responses of z-bar functions of said color-matching functions.

11. The color detector of claim 10, wherein at least two of said second order filters are in optical communication with a same photodetector.

12. The color detector of claim 10, wherein said second order filters are fabricated from at least two layers having a varied thickness.

13. The color detector of claim 10, wherein said second order filters are in optical communication with at least half of said photodetectors.

14. The color detector of claim 1, wherein said bandwidth of each filter is configured to correspond to a peak wavelength of a curve from a set of standard color matching functions.

15. The color detector of claim 1, wherein said bandwidths of said filters match said curves of said color-matching functions by at least 90 percent.

16. A color detector, comprising:
    a light source configured to generate light with a spectrum of wavelengths;
    a plurality of Fabry-Perot filters in optical communication with said light source, wherein each filter is configured to pass a bandwidth of wavelengths around a different peak wavelength;
    said plurality of Fabry-Perot filters being fabricated from at least one common layer of material of varied thickness;
    a plurality of photodetectors, each configured to receive light passed through a respective filter of said plurality of filters; and
    wherein said bandwidth of each filter is made to match a bandwidth of a curve from Commission Internationale de l'Eclairage (CIE) color-matching functions.

17. A method for improving color detection accuracy in a color detector comprising:
    matching a bandwidth passed by each of a plurality of color filters with a bandwidth of a Commission Internationale de l'Eclairage (CIE) color matching function; and
    separately detecting an amount of light passed by each said filter.

18. The method of claim 17, wherein said filters are first and second order Fabry-Perot filters.

19. The method of claim 17, further matching a peak wavelength passed by each of said plurality of color filters with a peak wavelength of a CIE color matching function.

20. The method of claim 19, further comprising optimizing centering and spacing of said variation in thickness using Monte Carlo analysis.

* * * * *